United States Patent
Bruemmer et al.

(10) Patent No.: US 9,341,343 B2
(45) Date of Patent: May 17, 2016

(54) PHOSPHOR DEVICE AND LIGHTING APPARATUS COMPRISING THE SAME

(75) Inventors: Mathias Bruemmer, Wusterwitz (DE); Ulrich Hartwig, Berlin (DE); Nico Morgenbrod, Berlin (DE); Matthias Morkel, Berlin (DE); Henning Rehn, Berlin (DE)

(73) Assignee: OSRAM GmbH, Munich (DE)

( * ) Notice: Subject to any disclaimer, the term of this patent is extended or adjusted under 35 U.S.C. 154(b) by 85 days.

(21) Appl. No.: 13/818,542

(22) PCT Filed: Aug. 24, 2010

(86) PCT No.: PCT/EP2010/062339
§ 371 (c)(1),
(2), (4) Date: May 10, 2013

(87) PCT Pub. No.: WO2012/025147
PCT Pub. Date: Mar. 1, 2012

(65) Prior Publication Data
US 2014/0153214 A1    Jun. 5, 2014

(51) Int. Cl.
| | | |
|---|---|---|
| *F21V 9/16* | (2006.01) | |
| *F21V 13/08* | (2006.01) | |
| *A61B 1/06* | (2006.01) | |

(Continued)

(52) U.S. Cl.
CPC ............... *F21V 13/08* (2013.01); *A61B 1/0653* (2013.01); *F21K 9/56* (2013.01); *F21V 29/502* (2015.01); *G03B 21/204* (2013.01); *H04N 9/315* (2013.01);

(Continued)

(58) Field of Classification Search
CPC ......... F21V 13/08; F21V 29/502; F21V 9/16; F21K 9/56; H04N 9/315; H04N 9/3158; A61B 1/0653; G03B 21/204; H01L 33/504; G21K 4/00; G21K 2004/06
USPC .............. 362/84, 259, 277; 250/483.1–488.1; 359/884; 428/690
See application file for complete search history.

(56) References Cited

U.S. PATENT DOCUMENTS 7,070,300 B2 *  7/2006  Harbers et al. ................ 362/231
7,445,340 B2 * 11/2008  Conner et al. .................. 353/20

(Continued)

FOREIGN PATENT DOCUMENTS

| DE | 10 2007 037875 | 2/2009 |
| JP | 2005-304621 | 11/2005 |

(Continued)

OTHER PUBLICATIONS

English translation of WO2009/021859 to Berben.*

*Primary Examiner* — Anne Hines
*Assistant Examiner* — Jose M Diaz
(74) *Attorney, Agent, or Firm* — Cozen O'Connor

(57) ABSTRACT

A phosphor device (1) comprising a carrier member (2) having upper and lower faces; a phosphor layer (3) being arranged at the upper face of the carrier member (2), whereby the phosphor layer (3) comprises at least one phosphor zone (R; G; Y); a reflective zone (33) being arranged adjacent to the at least one phosphor zone (R; G; Y); an optical transmitting member (4) having a first end face (7) and a second end face (9), the optical transmitting member (4) being arranged at the top portion of the phosphor layer (3) and the reflective zone (33), whereby wherein the first end face (7) of the optical transmitting member (4) covers at least a subarea (8) of each of the at least one phosphor zone (R; G; Y) and the reflective zone (33).

17 Claims, 2 Drawing Sheets

(51) Int. Cl.
  *G03B 21/20* (2006.01)
  *H04N 9/31* (2006.01)
  *F21K 99/00* (2016.01)
  *F21V 29/502* (2015.01)
  *H01L 33/50* (2010.01)

(52) U.S. Cl.
  CPC ............... *H04N 9/3158* (2013.01); *F21V 9/16* (2013.01); *H01L 33/504* (2013.01)

(56) References Cited

U.S. PATENT DOCUMENTS

| | | | |
|---|---|---|---|
| 7,540,616 B2 * | 6/2009 | Conner | 353/20 |
| 7,651,243 B2 * | 1/2010 | McGuire et al. | 362/293 |
| 7,942,537 B2 * | 5/2011 | Krijn et al. | 362/19 |
| 8,496,352 B2 * | 7/2013 | Bartlett | 362/259 |
| 8,662,672 B2 * | 3/2014 | Hikmet et al. | 353/31 |
| 8,827,475 B2 * | 9/2014 | Parker et al. | 362/84 |
| 2002/0123666 A1 | 9/2002 | Matsumoto | |
| 2003/0218880 A1 * | 11/2003 | Brukilacchio | 362/293 |
| 2004/0047162 A1 * | 3/2004 | Saccomanno et al. | 362/558 |
| 2005/0007767 A1 * | 1/2005 | Fischer et al. | 362/157 |
| 2005/0270775 A1 | 12/2005 | Harbers et al. | |
| 2006/0238545 A1 * | 10/2006 | Bakin et al. | 345/613 |
| 2007/0024971 A1 * | 2/2007 | Cassarly et al. | 359/487 |
| 2007/0146639 A1 * | 6/2007 | Conner | 353/20 |
| 2008/0170392 A1 * | 7/2008 | Speier et al. | 362/227 |

FOREIGN PATENT DOCUMENTS

| | | |
|---|---|---|
| JP | 2008-43754 | 2/2008 |
| TW | 201028588 | 8/2010 |
| WO | WO 2009/021859 | 2/2009 |
| WO | WO 2009/047683 | 4/2009 |
| WO | WO 2010/067291 | 6/2010 |
| WO | WO 2010/090862 | 8/2010 |

* cited by examiner

PHOSPHOR DEVICE AND LIGHTING APPARATUS COMPRISING THE SAME

RELATED APPLICATIONS

This is a U.S. national stage of application No. PCT/EP2010/062339, filed on Aug. 24, 2010.

FIELD OF THE INVENTION

The invention relates to a phosphor device. Furthermore, the invention relates to a lighting apparatus comprising such phosphor device and a method of operation of the lighting apparatus including said phosphor device.

BACKGROUND OF THE INVENTION

Phosphor devices are used in lighting apparatus wherein the phosphor (component or mixture), i.e. a substance with wavelength-converting properties, e.g. a fluorescent or luminescent substance, is remote from the exciting light source. Therefore, they are also called remote phosphor devices. Remote phosphor devices can be used in various lighting applications, e.g. in RGB projection equipment, generating red (R), green (G) and blue (B) light for coloured video projection. Other possible lighting applications comprise medical, architectural or entertainment lighting with coloured or white light.

In prior art remote phosphor devices, such as phosphor wheels, the phosphor is coated on a carrier plate. The phosphor is excited by exciting light, e.g. visible blue laser light (450 nm), impinging on the phosphor layer. The exciting laser light is wavelength-converted by the phosphor to generate light with longer wavelengths (e.g. broad spectral distribution with a peak at approximately 520 nm for green light).

The wavelength-converted light from the phosphor is collected by an optical transmitting member, e.g. an optical collimator such as a lens made of glass, arranged in front of the phosphor.

SUMMARY OF THE INVENTION

It is an object of the present invention to provide an alternative phosphor device. It is a further object of the present invention to provide a phosphor device with enhanced capabilities for tailoring the spectral properties of the wavelength-converted light emitted by said phosphor device.

According to one aspect of the present invention, adjustment of the colour of the wavelength-converted light is provided.

Another aspect of the present invention is to provide adjustment of the colour temperature of the wavelength-converted white light.

Another aspect of the present invention is to provide adjustment of the colour rendering of the wavelength-converted white light.

The object of the present invention is achieved by a phosphor device comprising: a carrier member having upper and lower faces; a phosphor layer being arranged at the upper face of the carrier member, whereby the phosphor layer comprises at least one phosphor zone; a reflective zone being arranged adjacent to the at least one phosphor zone; an optical transmitting member having a first end face and a second end face, the optical transmitting member being arranged at the top portion of the phosphor layer and the adjacent reflective zone, whereby the first end face of the optical transmitting member covers at least a subarea of each of the at least one phosphor zone and the reflective zone.

Another aspect of the present invention is directed to for a lighting apparatus comprising the phosphor device according to an embodiment of the present invention. Finally, another aspect of the present invention is directed to a method of operation of the lighting apparatus comprising the phosphor device according to an embodiment of the present invention.

According to an embodiment of the present invention, the phosphor layer comprises at least one phosphor zone. Furthermore, a reflective zone is arranged adjacent to the at least one phosphor zone. The at least one phosphor zone serves the purpose of wavelength-converting the exciting light impinging on the phosphor. The reflective zone, however, reflects the exciting light without converting its wave-length. In other words, due to the reflective zone, a fraction of the exciting light is directly usable for mixing with the wavelength-converted light, i.e. without being wavelength-converted prior to the mixing. The exciting light may be visible electromagnetic radiation (VIS), e.g. blue light, as well as ultraviolet (UV) or infrared radiation (IR).

The at least one phosphor zone comprises a phosphor component, e.g. a phosphor for emitting red (R), green (G) or yellow light (Y), or a phosphor mixture, e.g. a white light emitting phosphor mixture. Furthermore, the properties of a phosphor mixture may vary within a phosphor zone.

The phosphor layer may be subdivided into two or more phosphor zones. In this case, the phosphor zones may be separated from each other by division bars, preventing crosstalk of the light between the individual phosphor zones. This may also be accomplished by embedding each individual phosphor zone separately into the carrier member. Preferably, the division bars, if any, are as narrow as possible to maximize the optical efficiency of the device.

The spectral properties of the light, mixed from wavelength-converted light and directly reflected exciting light, may be adjusted by adjusting the proportions of the subareas of the phosphor zones (R,G) and the reflective zone irradiated by the exciting light.

In an embodiment designed for exciting with blue light (B), e.g. 450 nm laser light, the phosphor layer is a single phosphor zone consisting of a phosphor for emitting yellow light (Y). The wavelength-converted yellow light is mixed with the directly reflected blue light inside the optical transmitting member resulting in white light (BY). This embodiment is particularly suitable for white light illumination applications.

In another embodiment designed for exciting with blue light (B), e.g. 450 nm laser light, the phosphor layer comprises a first phosphor zone consisting of a phosphor for emitting red light (R) and a second phosphor zone consisting of a phosphor for emitting green light (G). The wavelength-converted red and green light is mixed with the directly reflected blue light inside the optical transmitting member resulting in white light (RGB). This embodiment is particularly suitable for RGB-projection applications, and also for other white light illumination applications. Preferably, the area of the first end face of the optical transmitting member is smaller than the total area of the phosphor layer and the reflective zone. The exciting light, impinging from the first end face of the optical transmitting member, is wavelength-converted by the phosphor(s) of that particular partial area of the phosphor layer, which is irradiated by the exciting light. Furthermore, a fraction of the impinging exciting light is directly reflected by that particular partial area of the reflective zone, which is irradiated by the exciting light. Preferably, the first end face is as close as possible to the surface of the phosphor layer and the reflective zone to minimize optical losses. Therefore, the sum of the partial areas of the phosphor layer and the reflective zone, irradiated by the exciting light, is virtually equal to the area of the first end face of the optical transmitting member, projected on the phosphor layer.

Exciting only a partial area of the phosphor layer and the reflective zone allows for adjusting the spectral properties of the phosphor device by selecting appropriate positions of the first end face of the optical transmitting member on the phosphor layer and the reflective zone. An appropriate position may be defined by covering subareas of the phosphor zone(s) and the reflective zone such that a particular colour of the mixed wavelength-converted light is achieved. Another appropriate position may be defined by covering subareas of the zones, e.g. comprising red light and green light phosphors with blue exciting light or white light phosphor mixtures, such that a particular colour temperature or CRI value of the mixed wavelength-converted white light is achieved.

Furthermore, the phosphor zone(s) and the reflective zone are preferably designed such that the respective subareas of the zones covered by the first end face of the optical transmitting member vary in at least one direction of a relative movement between phosphor layer and optical transmitting member. This concept allows for adjusting the relative proportions of the subareas covered by the first end face of the optical transmitting member and, hence, the spectral properties of the mixed light. The mixed light consist of the light wavelength-converted by the excited subareas of the phosphor zone(s) and the exciting light directly reflected by the irradiated subareas of the reflective zone. For example, the zones may be formed as stripes tapered or stepped in the direction of relative movement. This concept will be explained later with reference to the drawings in more detail.

Preferably, the phosphor device is configured to enable relative lateral movement between the first end face of the optical transmitting member and the phosphor zone(s) including the reflective zone. This may be conducted by translational and/or rotational motion of the optical transmitting member over the phosphor layer and the reflective zone or vice versa. This allows not only for presetting a favoured spectral property of the phosphor device during its manufacturing, but also adjusting another spectral property during operation or even readjusting to compensate degradation of the phosphor (s) of the phosphor device. To this end, the relative position may be controlled and adjusted by sensing the resulting light colour in order to achieve a particular target value.

The light, wavelength-converted by the excited subarea of the or each phosphor zone, and the light directly reflected from the reflective zone is collected and mixed by the optical transmitting member. The optical transmitting member is designed to transmit the light, entering through one end face and leaving through the other end face, by refraction and/or (internal) reflexion. Preferably, the optical transmitting member is elongated and has a polygonal cross section, particularly a triangle or a rectangle. Such a shape of the optical transmitting member allows for proper spatial mixing of the light collected from the irradiated subareas of the respective zones. On the contrary, a circular cross section or, similarly, a polygonal cross section with many corners, thereby approximating a circular cross section, may result in poor light mixing, i.e. colour fringes when transmitted to a target area or even the perceptibility of the irradiation pattern of the zones. The mixing of the wavelength-converted light may be further improved by arranging multiple phosphor zones of the same converting colour alternating with phosphor zones of another converting colour, e.g. RGRGR, or RGGBRGGB etc.

The carrier member may be a solid body, e.g. a plate, a block or the like. Particularly, the carrier member may be made from a material with suitable cooling properties, e.g. a metal such as copper, aluminum or the like, facilitating dissipation of the heat generated by the exciting light when impinging on the phosphor layer. Due to the solid body, the wavelength-converted light is re-fleeted off the phosphor device and collected and mixed by the optical transmitting member, together with the directly reflected light. The optical reflectivity of the surface of the carrier member beneath the phosphor layer may be improved, e.g. polished, to enhance the efficiency of the wavelength-conversion. The same also applies to the surface of the reflective zone to enhance the efficiency of the directly reflected exciting light. The base area of the carrier member may have various shapes, e.g. rectangular or circular. Furthermore, the surface of the carrier member on which the phosphor layer and the reflective zone are arranged may be flat or curved.

The phosphor device according to the present invention may be part of a lighting apparatus, further comprising an exciting light source, e.g. a laser, preferably a laser diode or a laser diode array, for emitting exciting light. The exciting light enters the phosphor device through the second end face of the optical transmitting member. After passing through the first end face of the optical transmitting member a first fraction of the exciting light impinges on the phosphor zone(s) of the phosphor layer and the other fraction of the exciting light impinges on the reflective zone. The first fraction of the exciting light is reflected back after being wavelength-converted by the irradiated phosphor (s) of the phosphor zone(s). The other fraction of the exciting light is directly reflected back by the reflective zone.

Both fractions of the reflected light are collected and mixed by the optical transmitting member after entering its first end face. Thereafter, the mixed light leaves the optical transmitting member through the second end face. Furthermore, the mixed light may be guided and shaped by additional optical devices for further use in various applications. Further details will be explained in the description of the drawings.

BRIEF DESCRIPTION OF THE DRAWINGS

Embodiments of the present invention will now be described, by way of example, with reference to the accompanying drawings in which:

FIG. 1b is a top view of the embodiment shown in FIG. 1a;

FIG. 2b is a sectional view of the carrier member shown in FIG. 2a;

PREFERRED EMBODIMENTS OF THE INVENTION

Figure 1A:
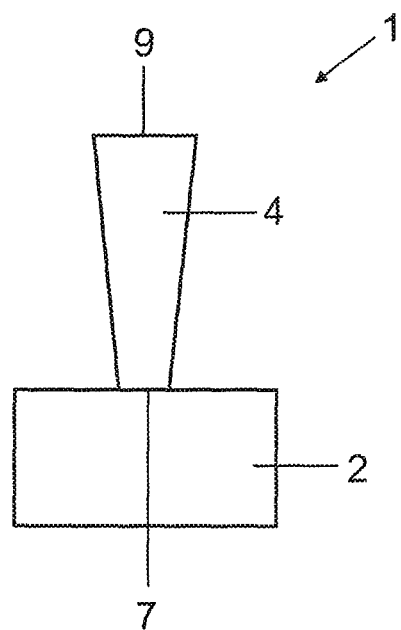
FIG. 1a is a side view of an embodiment of a phosphor device according to the present invention.

In the attached drawings, showing different embodiments of the present invention, the same reference numerals are used for the same or similar features.

Figure 1B:
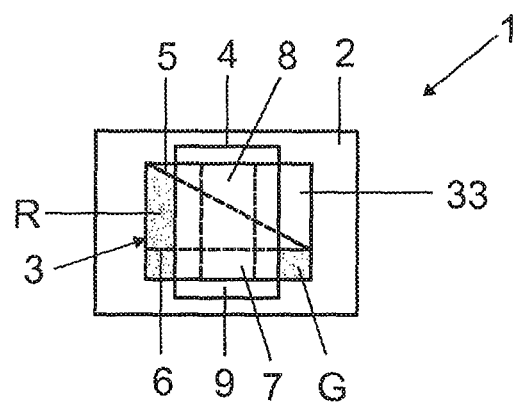
Figure 2A:
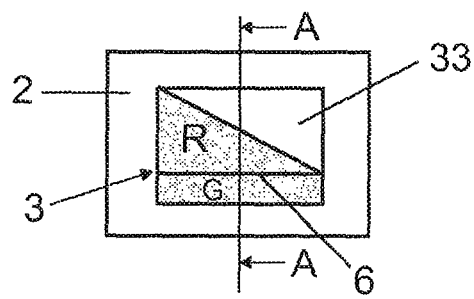
FIG. 2a is a top view of the carrier member with the phosphor layer and reflective zone shown in FIGS. 1a, 1b.
Figure 2B:
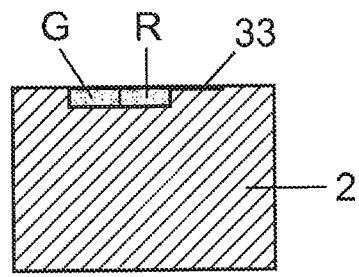

As schematically shown in FIGS. 1a and 1b, a first embodiment of a phosphor device 1 is constructed having a carrier member 2 made of aluminium, a phosphor layer 3, embedded at the upper face of the carrier member 2, a reflected zone 33 polished on a surface area adjacent to the phosphor layer 3 and an optical transmitting member 4 made of optical glass, preferably quartz glass or BK7 (index of refraction is 1.46 and 1.52, respectively), arranged on the top portion of the phosphor layer 3. Due to the good cooling properties of aluminium, the carrier member 2 also functions as a cooling member. The phosphor layer 3 and the adjacent reflective zone 33 altogether have a rectangular base area of about 2×10 mm2. If an immersion layer is used on top of the phosphor layer, both optically effective lengths are reduced (divided by the index of refraction of the immersion layer). Typical values for the thickness of the phosphor layer and immersion layer are approximately 0.1 mm for total conversion after double transit of the exciting light according to the reflective mode. The surface portion of the upper face of the carrier member 2 underneath the embedded phosphor layer 3 is polished to enhance its reflectivity. In the following description, reference is also made to FIGS. 2a, 2b, showing, for the sake of clarity, only the carrier member 2 including the phosphor layer 3 and the reflective zone 33 in a top view and a sectional view along the cutting plane AA, respectively. The phosphor layer 3 is subdivided into two phosphor zones R, G separated like tiles by a thin division bar 6. The first phosphor zone R comprises a phosphor for emitting red light, e.g. Eu doped YAG. The second phosphor zone G comprises a phosphor for emitting green light, e.g. Ce doped YAG. This configuration of the phosphor layer 3 is designed for irradiating with blue light, e.g. 450 nm laser light, whereby a fraction of the blue light is directly reflected by the reflective zone 33. In different lateral positions of the first end face 7 of the optical transmitting member 4, being in close contact with and covering partial areas 8 of the top portion of phosphor layer 3 and the reflective zone 33, different proportions of subareas of the phosphor zones R, G and the reflective zone 33 can be irradiated by the blue exciting light. According to the proportions of the irradiated subareas, different colours of the light mixed from the wavelength-converted red and green light and the directly reflected blue light can be achieved. Furthermore, different corrected colour temperatures CCT and colour rendering indices CRI of the resulting mixed white light RGB can be achieved. The following table shows various corresponding colour temperatures CCT, the proportions of the subareas R, G, B (B: reflected 450 nm exciting laser light) required to achieve the CCT values and the resulting CRI values (phosphor conversion efficiencies neglected):

CCT [K] R [%] G [%] B [%] CRI
2700 69,28 24,33 6,39 74
3000 65,27 26,06 8,67 76
3500 59,48 28,05 12,47 79
4000 54,68 29,27 16,05 82
4500 50,72 29,98 19,31 84
5000 47,45 30,36 22,20 85
5500 44,73 30,52 24,75 87
6000 42,46 30,56 26,98 87
6500 40,54 30,51 28,95 88
8000 36,36 30,15 33,50 89

Furthermore, due to the excellent mixing properties of the tapered optical transmitting member 4, having a rectangular cross-section, the colour distribution of the mixed light passing through the second end face 9 of the optical transmitting member 4 is remarkably uniform. The phosphor device 1, schematically shown in FIGS. 1a, 1b, may further comprise additional means for enabling and controlling the relative lateral motion between optical transmitting member on the one hand and phosphor layer and reflective zone on the other hand, but which are not shown for the sake of clarity.

The whole setup is designed for projection purposes illuminating a 0.55" digital mirror device (DMD, also known as Digital Light Processing Unit—DLP®—by Texas Instruments) having an acceptance angle of 12° (half-angle). Therefore, the wavelength-converted light leaving the optical transmitting member should have an angular distribution of below 12°. This is accomplished by the conical transmitting member having a rectangular cross section and a length of approximately 50 to 80 mm. The first end face 7 of the optical transmitting member 4 has a rectangular base area of approximately 2.32×1.74 mm2 (aspect ratio 4:3). The size of the other end face of the transmitting member is then determined according to the Etendue preservation theorem, resulting in 11.2×8.4 mm2.

For other lighting applications, the setup has to be adapted to the specific optical requirements. For instance, for medical endoscopy using fibre bundles of 4.8 mm diameter the acceptance angle is 22° (half-angle) and the aperture is 18.1 mm2. In the case of a Lambertian distribution of the wavelength-converted light, this transforms into a maximum usable area of 2.53 mm2 for the entrance face. This corresponds to an area of 1.4×1.4 mm2 for the first end face of the optical transmitting member having a square cross section. The length of the optical transmitting member may be 25 to 50 mm. For applications using a light guide of 4.8 mm diameter having an acceptance angle of 30° (half-angle), e.g. for automobile head lights, the maximum usable area for the entrance face is 4.5 mm2. This corresponds to an area of 1.75×1.75 mm2 for a square first end face of the optical transmitting member. The length of the optical transmitting member, having a circular second end face, may be 20 to 40 mm.

Figure 3:
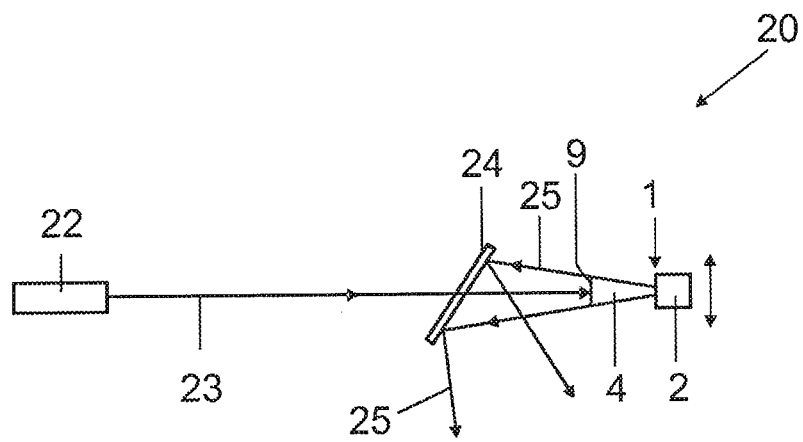
FIG. 3 is a schematic view of a lighting apparatus comprising a phosphor device as shown in FIGS. 1a, 1b.

FIG. 3 shows a schematic view of a lighting apparatus 20 comprising a phosphor device 1 as shown in FIGS. 1a, 1b. The lighting apparatus 20 may be used for projection applications. The lighting apparatus 20 further comprises at least one laser diode 22, emitting exciting light 23 of a wavelength of about 450 nm, and a dichroitic mirror 24 arranged on the optical axis between the laser diodes 22 and the phosphor device 1. For high power applications, the exciting light source may be a laser array with more than 1 W. The maximum useable laser power may be restricted by degradation of the phosphor layer due to excessive laser power density. The exciting light 23 passes through the dichroitic mirror 24, enters the phosphor device 1 through the second end face 9 of the optical transmitting member 4 and is received by the phosphor layer and the reflective zone (not shown) arranged on the upper face of the carrier member 2. Depending on the position of the first end face of the optical transmitting member 4 on the phosphor layer and the reflective zone, the light wavelength-converted by the excited subareas of the phosphor zones R, G and the light directly reflected by the reflective zone is collected and mixed by the optical transmitting member 4, resulting in mixed light with particular spectral properties. If desired, the spectral properties of the mixed light may be adjusted by relatively moving the optical transmitting member and the phosphor layer including the reflective zone. The mixed light exits the second end face 9 of the optical transmitting member 4 and is transmitted to the dichroitic mirror 24. The dichroitic mirror 24 is tilted to reflect the mixed wavelength-converted light off the optical axis defined by the beam of the diode laser 22. Depending on the specific application, further optical elements may be involved.

Figure 4:
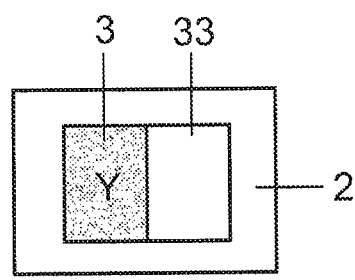
FIG. 4 shows a top view of another embodiment of a carrier member with a phosphor layer and a reflective zone according to the present invention.

A top view of an alternative embodiment of the phosphor device 1 is schematically shown in FIG. 4 (optical transmitting member is not shown for the sake of clarity). The phosphor layer 3 embedded on the upper face of the carrier member 2 consists of only one phosphor zone Y made of a phosphor for emitting yellow light, e.g. YAG:Ce. This configuration of the phosphor layer 3 is also designed for irradiating with blue light, e.g. 450 nm laser light, whereby a fraction of the blue light is directly reflected by the reflective zone 33. The yellow light, wavelength-converted by the phosphor of the phosphor zone Y, and the blue light, directly reflected by the reflective zone 33, is collected and mixed by the optical transmitting member (not shown) resulting in white light (BY). The first end face of the optical transmitting member corresponds to the total area of the phosphor zone Y and the reflective zone 33, because this embodiment is designed for a fixed position of the optical transmitting member.

The scope of protection of the invention is not limited to the examples given hereinabove. The invention is embodied in each novel characteristic and each combination of characteristics, which includes every combination of any features which are stated in the claims, even if this feature or combination of features is not explicitly stated in the examples.

The invention claimed is:

1. A phosphor device comprising:
    a carrier member having upper and lower faces;
    a phosphor layer arranged at the upper face of the carrier member, whereby the phosphor layer comprises at least one phosphor zone;
    a reflective zone arranged adjacent to the at least one phosphor zone;
    an optical transmitting member having a first end face that faces the upper face of the carrier member and a second end face that receives exciting light from a light source, each of the first and second end faces having a same polygonal shape, the second end face having a greater area than the first end face, the optical transmitting member being arranged at the top portion of the phosphor layer and the reflective zone,
    wherein the first end face of the optical transmitting member covers at least a subarea of each of the at least one phosphor zone and the reflective zone,
    wherein the optical transmitting member is elongated and has a polygonal cross section over its entire length, a shape of the cross section corresponding to the polygonal shape of the first and second end faces, and
    wherein a width of the polygonal cross section of the optical transmitting member decreases linearly in a direction approaching the carrier member.

2. The phosphor device according to claim 1, wherein the at least one phosphor zone comprises a phosphor component or a phosphor mixture.

3. The phosphor device according to claim 2, wherein the phosphor component is any member of the following group: a phosphor for emitting red light, a phosphor for emitting green light, a phosphor for emitting yellow light.

4. The phosphor device according to claim 2, wherein the phosphor mixture is suitable for emitting white light.

5. The phosphor device according to claim 1, comprising two or more phosphor zones, wherein the phosphor zones are separated from each other by division bars.

6. The phosphor device according to claim 5, wherein the phosphor zones are individually embedded into the carrier member.

7. The phosphor device according to claim 1, wherein the phosphor device is configured to enable relative lateral movement between the first end face of the optical transmitting member and the at least one phosphor zone and the reflective zone.

8. The phosphor device according to claim 7, wherein the at least one phosphor zone and the reflective zone are configured such that the proportions of the subareas of the zones covered by the first end face of the optical transmitting member change in directions of the relative movement.

9. A lighting apparatus comprising:
    a phosphor device according to claim 1;
    an exciting light source for emitting the exciting light;
    wherein the phosphor device and the exciting light source are arranged such that the exciting light is enabled to enter the phosphor device through the second end face of the optical transmitting member.

10. The lighting apparatus according to claim 9, wherein the exciting light source comprises a laser light source.

11. A method of operation of a lighting apparatus according to claim 9 comprising the following steps:
    positioning the optical transmitting member such that at least subareas of the at least one phosphor zone of the phosphor layer and the adjacent reflective zone are covered by the first end face of the optical transmitting member; and
    guiding the exciting light for entering the optical transmitting member through its second end face and for impinging on the phosphor layer and the reflective zone through its first end face.

12. The method according to claim 11, further comprising the steps of collecting and mixing the light, wavelength-converted by the area of the phosphor layer irradiated by the exciting light, and the exciting light directly reflected by the reflective zone with the optical transmitting member.

13. The method according to claim 12, further comprising the step of moving the optical transmitting member over the surface of the phosphor layer and the adjacent reflective zone for adjusting the properties of the mixed light, thereby covering various subareas of the phosphor zones of the phosphor layer and the reflective zone, resulting in various proportions of irradiated subareas of the phosphor zones and the reflective zone, respectively.

14. The method according to claim 11, further comprising the steps of sensing the resulting light colour or corrected colour temperature and controlling and adjusting the relative position of the optical transmitting member if necessary to achieve a target value.

15. The phosphor device according to claim 1, wherein the optical transmitting member is shaped to mix light emitted from the at least one phosphor zone and light reflected by the reflective zone.

16. The phosphor device according to claim 1, wherein the same polygonal shape of the first and second end faces is one from the group consisting of a rectangle and a triangle.

17. The phosphor device according to claim 1, wherein an aspect ratio of the same polygonal shape of the first end face and the second end face are identical.

* * * * *